April 4, 1939. B. RUYS Plant Pat. 324
DELPHINIUM
Filed Sept. 13, 1938
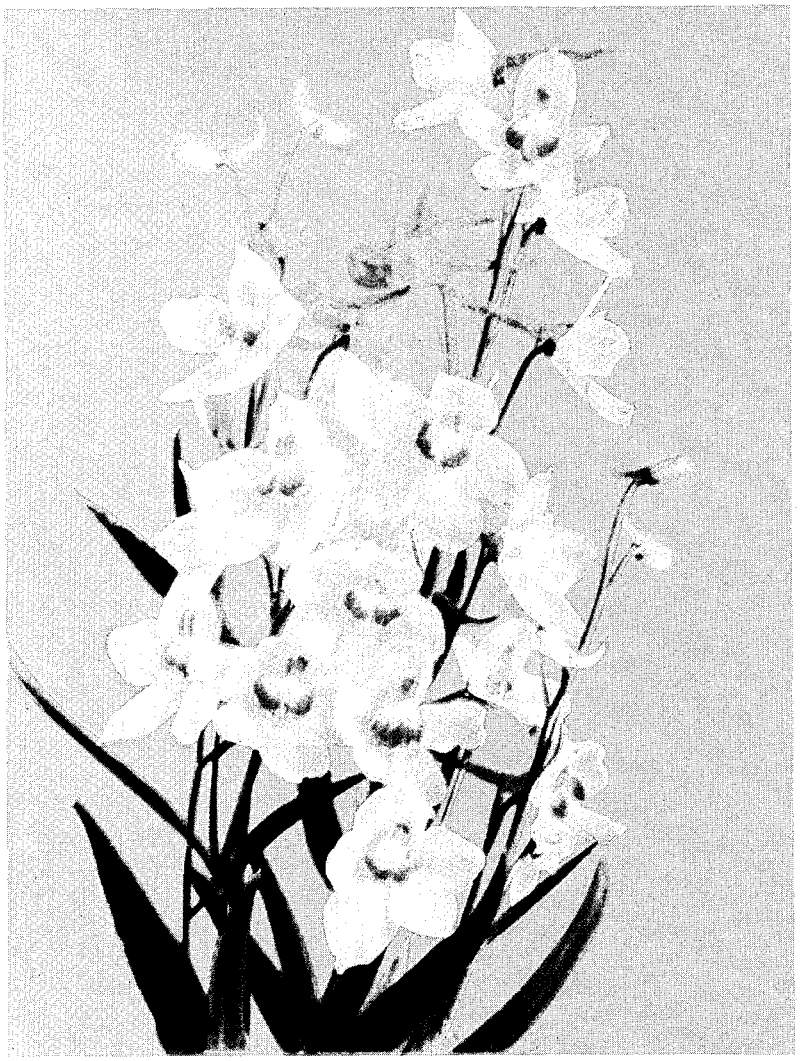
Inventor
B. Ruys
By Robbins & Robbins
Attorneys Patented Apr. 4, 1939

Plant Pat. 324

UNITED STATES PATENT OFFICE

324

DELPHINIUM

Bonne Ruys, Dedemsvaart, Netherlands, assignor to Jackson & Perkins Company, Newark, N. Y.

Application September 13, 1938, Serial No. 229,780

1 Claim. (Cl. 47—60)

This discovery relates to a new and distinct variety of delphinium, a hybrid of *Delphinium nudicaule*, but differing in material respects from its parents.

The variety originated as a chance seedling, the result of a cross of *Delphinium nudicaule* and an unknown variety, said seedling being superior to and different in color, vigor or growth, size of flower spike, foliage, root system and method of reproduction from its parents. It is also characterized as to novelty by its earliness and floriferousness.

The novelty and distinctiveness of this new plant variety may best be understood by comparison with its parent, *Delphinium nudicaule*. First and most important is the color of its flower, which has pink sepals and violet petals, whereas the parent variety has orange sepals and yellow petals.

In vigor of growth this new variety has the true hybrid vigor and grows from 4 to 6 feet tall, whereas *Delphinium nudicaule* grows only from 1 to 1½ feet, and the size of the flower spike differs in that it is proportionately larger and fuller.

It may be noted further as regards its habit of growth that instead of the plant top disappearing and the plant going dormant for quite a while in the summer, as is the habit of *nudicaule*, the new variety immediately starts the new shoots even before the flower is through blooming, and it is never without foliage.

In the section of northern New York, the variety blooms three and sometimes four times and is very frost resistant at the end. This habit greatly enhances the value of the variety as a garden plant.

The foliage of the new variety differs in form and also in texture, being non-succulent or slightly succulent, and the form varies slightly in contour.

It is also notable that the new variety has a different root system—many fibrous roots, whereas the *Delphinium nudicaule* has a fleshy root.

The new variety has been asexually reproduced and comes true to form, but thus far it has not been possible to reproduce it from seed, thus marking another point of distinctiveness. It has been known to seed in very rare instances, but the seedlings were entirely different from the parents.

The following is a detail description of the new variety, the color terminology being in accord with Ridgway's Color Standard:—

Parentage:

*Seed parent.*—*Delphinium nudicaule.*

*Pollen parent.*—Unknown.

Classification:

*Botanic and commercial.*—*Delphinium hybrid.*

Bloom:

*Type.*—Similar to *Delphinium belladonna;* 3–4 cm. flowers in a tall (3″–6″) open, but many flowered raceme.

*Bud.*—Color—Javel Green (Plate V), tipped Cameo Pink (Plate XXVI), ovoid spurred Manganese Violet (Plate XXV).

*Flower.*—Sepals—5 (four uniform). Color—Deep Rose Pink (Plate XII); outside Thulite Pink (Plate XXVI); green spot each sepal—size 1.5 to 1.8 cm. Shape—4 uniform sepals, linear to ovate; 1 spurred longer than the uniform. Surface—netted veined, slightly pilose; inner surface glabrous. Color: inner surface—Deep Rose Pink (Plate XII); outer tube—Citron Green (Plate XXXI) to Cameo Pink (Plate XXVI). Petals—4, 5–7 mm. long; upper two cleft spatulate, Manganese Violet (Plate XXV) with Chartreuse Yellow (Plate XXXI), spurs extending into sepal, spur lower, two spatulate 5–7 mm., Manganese Violet (Plate XXV), bearded outer surface, slightly pilose, inner surface glabrous. Carpels—3; surface smooth, form curved. Stamens—numerous; conspicuous in opening flower. Bracteoles—in pairs, linear, slightly pilose; somewhat remote (5 mm.) from flower. Bracts: lower surface—Cress Green (Plate XXXI); upper surface—Dark Cress Green (Plate XXXI). 3–5 cm. or more, lanceolate, pubescent to dense pilose.

Plant:

*Form.*—Bush.

*Growth.*—Very vigorous, upright, branching. Repeats with new flower shoots at least three times a year.

*Stem.*—Bice Green (Plate XVII), pulverulent. Long, 4′–6′, erect leaves and loose, many flowered raceme, striate, glabrous to sparsely pilose in raceme. Side branches brittle.

*Foliage.*—Size—8–12 cm. Quantity—normal. Color: new foliage:—upper side and under side—Bice Green (Plate XVII). Old foliage: — upper side — Cress Green (Plate XXXI); under side—Light Cress Green (Plate XXXI). Shape—palmate, 5–7 lobed. Texture: upper side and under side—hirsute; ribs and veins—prominent. Edge—smooth, secondary lobed. Rachis—Light Cress Green (Plate XXXI); slightly hirsute. Disease resistance—very resistant.

*Roots.*—Fibrous.

*Seed.*—The variety is self sterile and although repeatedly tried has not reproduced itself from seed.

I claim:

A new and distinct variety of delphinium, characterized by the form and habit of growth of the plant, its root system, and the pink color of its blossom, substantially as shown and described.

B. RUYS.